(12) United States Patent
Xu et al.

(10) Patent No.: US 12,089,864 B2
(45) Date of Patent: Sep. 17, 2024

(54) FLEXIBLE SURGICAL TOOL SYSTEM

(71) Applicant: BEIJING SURGERII ROBOTICS COMPANY LIMITED, Beijing (CN)

(72) Inventors: Kai Xu, Beijing (CN); Zhonghao Wu, Beijing (CN)

(73) Assignee: BEIJING SURGERII ROBOTICS COMPANY LIMITED, Beijing (CN)

( * ) Notice: Subject to any disclaimer, the term of this patent is extended or adjusted under 35 U.S.C. 154(b) by 730 days.

(21) Appl. No.: 17/292,557

(22) PCT Filed: Dec. 27, 2019

(86) PCT No.: PCT/CN2019/129291
§ 371 (c)(1),
(2) Date: May 10, 2021

(87) PCT Pub. No.: WO2020/135748
PCT Pub. Date: Jul. 2, 2020

(65) Prior Publication Data
US 2022/0000510 A1 Jan. 6, 2022

(30) Foreign Application Priority Data
Dec. 28, 2018 (CN) .......................... 201811619513.5

(51) Int. Cl.
*A61B 17/29* (2006.01)
*A61B 34/00* (2016.01)

(52) U.S. Cl.
CPC .............. *A61B 17/29* (2013.01); *A61B 34/71* (2016.02); *A61B 2017/2903* (2013.01); *A61B 2017/2905* (2013.01)

(58) Field of Classification Search
CPC . A61B 17/29; A61B 34/71; A61B 2017/2903; A61B 2017/2905
See application file for complete search history.

(56) References Cited

U.S. PATENT DOCUMENTS

| 5,297,443 A | 3/1994 | Wentz |
| 2002/0111621 A1 | 8/2002 | Wallace et al. |
| (Continued) | | |

FOREIGN PATENT DOCUMENTS

| CN | 101637402 A | 2/2010 |
| CN | 103085083 A | 5/2013 |
| (Continued) | | |

OTHER PUBLICATIONS

K Xu et al., "Development of the SJTU unfoldable robotic system (SURS) for single port laparoscopy" Transactions on Mechatronics, vol. 20, No. 5, pp. 2133-2145 (Oct. 1, 2015).

(Continued)

*Primary Examiner* — Brooke Labranche
(74) *Attorney, Agent, or Firm* — SZDC Law PC

(57) ABSTRACT

A flexible surgical tool system includes: a mechanical arm (10) comprising a first continuum segment (12), a rigid connection segment (13), and a second continuum segment (14), the first continuum segment (12), a rigid connection segment (13) and the second continuum segment (14) being sequentially associated to form a dual continuum mechanism; a surgical effector (50) connected at distal end of the second continuum segment (14); a transmission driving unit (20) associated with the rigid connection segment (13) and with a surgical effector (50), respectively, and operable to drive the first continuum segment (12) to bend in any direction to drive the second continuum segment (14) to bend in an opposite direction, and to drive the surgical effector (50) to rotate in a first plane and/or open and close in a second plane. The flexible surgical tool system can be applied to a natural orifice or a single surgical incision of a human body and perform operations.

14 Claims, 6 Drawing Sheets

(56) References Cited

U.S. PATENT DOCUMENTS

| | | |
|---|---|---|
| 2003/0149338 A1 | 8/2003 | Francois et al. |
| 2005/0096694 A1 | 5/2005 | Lee |
| 2006/0079889 A1 | 4/2006 | Scott |
| 2013/0090763 A1* | 4/2013 | Simaan ............... B25J 19/025 700/258 |
| 2015/0352728 A1 | 12/2015 | Wang |
| 2017/0165010 A1 | 6/2017 | Chaplin et al. |
| 2017/0196546 A1 | 7/2017 | Lee |
| 2018/0049815 A1 | 2/2018 | Overmyer et al. |
| 2018/0214220 A1 | 8/2018 | Kan |

FOREIGN PATENT DOCUMENTS

| | | |
|---|---|---|
| CN | 104758012 A | 7/2015 |
| CN | 106175852 A | 12/2016 |
| CN | 106308935 A | 1/2017 |
| CN | 106361386 A | 2/2017 |
| CN | 106361386 A1 | 2/2017 |
| CN | 106361387 A | 2/2017 |
| CN | 107020620 A | 8/2017 |
| CN | 109009328 A | 12/2018 |
| CN | 109452976 A | 3/2019 |
| EP | 2666434 A1 | 11/2013 |
| WO | 2009094670 A1 | 7/2009 |
| WO | 2016035086 A2 | 3/2016 |

OTHER PUBLICATIONS

Xu Kai et al. "Development of the SJTU unfoldable robotic system (SURS) for single port laparoscopy", IEEE/ASME Transactions on Mechatronics, IEEE Service Center, Piscataway, NJ, US., vol. 20, No. 5, Oct. 1, 2015, pp. 2133-2145, XP011668013.

Jienan Ding et al., "Design, simulation and evaluation of kinematic alternatives for insertable robotic effectors platforms in single port access surgery", 2010 IEEE International Conference on Robotics and Automation: ICRA 2010; Anchorage, Alaska, USA, May 3-8, 2010, IEEE, Piscataway, NJ, USA, May 3, 2010, pp. 1053-1058, XP031743181.

Kai Xu et al., "System design of an insertable robotic effector platform for single port access (SPA) surgery", Intelligent Robots and Systems, 2009, IROS 2009, IEEE/RSJ International Conference On, IEEE, Piscataway, NJ, USA, Oct. 10, 2009, pp. 5546-5552, XP031580389.

* cited by examiner

FLEXIBLE SURGICAL TOOL SYSTEM

The present application is the U.S. National Phase of International Application No. PCT/CN2019/129291, filed on Dec. 27, 2019, which claims priority to Chinese patent application No. 201811619513.5, filed on Dec. 28, 2018, entitled "Flexible Surgical Tool System," which is incorporated herein by reference for all purposes as if fully set forth herein.

TECHNICAL FIELD

The disclosure relates to a medical instrument, in particular to a flexible surgical tool system based on a dual continuum mechanism.

BACKGROUND

Multi-port laparoscopic minimally invasive surgery plays an important role in surgical operations due to small wound and fast postoperative recovery. The conventional da Vinci surgical robot of Intuitive Surgical Inc. assists surgeons in completing the multi-port laparoscopic minimally invasive surgery, and gets great commercial success.

After the multi-port laparoscopic surgery, single-port laparoscopic surgery and non-invasive surgery through natural orifice are developed. They have smaller wound and faster postoperative recovery. But in single-port laparoscopic surgery and non-invasive surgery through the natural orifice, all surgical instruments including visual illumination module and surgical operating arm reach a surgical site through a single channel, which has strict requirements on preparation of surgical instruments. Distal structures of the present surgical instruments are mainly multiple rods hinged in serial and driven by pulling force of steal wires, so that distal instruments can bend at the hinges. Because the steel wire rope needs to be kept in a continuous tensioning state through pulleys, due to this driving manner, further miniaturization of the surgical instrument is difficult to achieve and movement performance of the surgical instrument is difficult to further improve.

Although the Intuitive Surgical Inc. recently launched da Vinci Single-site (SS-type da Vinci) surgical robot, the original rigid surgical instrument is changed into a semi-rigid surgical instrument, and a pre-bending sleeve is introduced, which, to a certain extent, improves the movement performance of the surgical instruments, but still cannot fundamentally solve the problems faced by the traditional surgical instruments.

SUMMARY

In view of the above problems, an objective of the present disclosure is to provide a flexible surgical tool system based on a dual continuum mechanism. The flexible surgical tool system can be applied to a natural orifice or a single surgical incision of a human body and perform operations.

To this end, present disclosure provides a flexible surgical tool system comprising: a mechanical arm comprising a first continuum segment, a rigid connection segment, and a second continuum segment, the first continuum segment and the second continuum segment being sequentially associated to form a dual continuum mechanism; a surgical effector connected at distal end of the second continuum segment; a transmission driving unit associated with the rigid connection segment and with a surgical effector, respectively, and operable to drive the first continuum segment to bend in any direction to drive the second continuum segment to bend in an opposite direction, and to drive the surgical effector to rotate in a first plane and/or open and close in a second plane.

In the flexible surgical tool system, preferably, the transmission driving unit comprises a plurality of linear motion mechanisms consisting essentially of a double-threaded rod, a first sliding block, and a second sliding block; the first continuum segment comprises a first continuum fixing disk and direction-controlling continuum structural bones, and the rigid connection segment comprises a rigid connection fixing disk; the direction-controlling continuum structural bones comprises a plurality of pairs, distal ends of each pair of direction-controlling continuum structural bones are connected with the rigid connection fixing disk, and proximal ends of each pair of direction-controlling continuum structural bones pass through the first continuum fixing disk and are connected with the first sliding block and the second sliding block, respectively.

In the flexible surgical tool system, preferably, the second continuum segment comprises a second continuum fixing disk and a plurality of dual continuum structural bones; distal end of each dual continuum structural bone is connected with the second continuum fixing disk, and proximal end of each dual continuum structural bone passes through the rigid connection fixing disk and is connected with the first continuum fixing disk.

In the flexible surgical tool system, preferably, the surgical effector comprises: a surgical effector base connected at distal end of the second continuum segment via a surgical effector connection block; a wrist rotation mechanism mounted on the surgical effector base and associated with the linear motion mechanism and driven by the linear motion mechanism to perform a rotational motion in the first plane; a forceps effector mounted on the wrist rotation mechanism and associated with the linear motion mechanism, forceps effector being capable of synchronously rotating along with the wrist rotation mechanism and driven by the linear motion mechanism to perform opening or closing motion in the second plane.

In the flexible surgical tool system, preferably, the wrist rotation mechanism comprises: a wrist rotator rotatably connected with the surgical effector base; surgical effector housings symmetrically mounted on both sides of the wrist rotator; a pair of wrist structural bones, wherein a first end of one of the wrist structural bones is connected with the first sliding block, a second end sequentially passes through the first continuum segment, the rigid connection segment and the second continuum segment and is connected with a side of the wrist rotator, a first end of the other wrist structural bone is connected with the second sliding block, and a second end of the other wrist structural bone sequentially passes through the first continuum segment, the rigid connection segment and the second continuum segment and is connected with another side of the wrist rotator.

In the flexible surgical tool system, preferably, the forceps effector comprises: forceps rotators, two forceps rotators being rotatably connected between the two surgical effector housings; effector jaws, two effector jaws being integrally connected with the two forceps rotators, respectively; steering pulleys, multiple sets of the steering pulleys being rotatably connected between the two surgical effector housings; forceps structural bones comprising two pairs of forceps structural bones, wherein a first end of one forceps structural bone of each pair is connected with the first sliding block, a second end sequentially passes through the first continuum segment, the rigid connection segment and the second continuum segment, is wound around a first set of steering pulleys and connected with a side of a corresponding forceps rotator, and wherein a first end of the other forceps structural bone is connected with the second sliding block, and a second end sequentially passes through the first continuum segment, the rigid connection segment and the second continuum segment, is wound around a second set of steering pulleys and is connected with another side of the corresponding forceps rotator.

In the flexible surgical tool system, preferably, the mechanical arm further comprises a rigid feed segment comprising a plurality of rigid feed segment spacer disks spaced at proximal side of the first continuum fixing plate; the first continuum segment further comprises a plurality of first continuum spacer disks spaced between a distal side of the first continuum fixing disk and a proximal side of the rigid connection fixing disk; the direction-controlling continuum structural bone, the wrist structural bone and the forceps structural bone sequentially pass through the rigid feed segment spacer disks and the first continuum spacer disks.

In the flexible surgical tool system, preferably, the rigid connection segment further comprises a plurality of rigid connection spacer disks spaced at distal side of the rigid connection fixing disk; the second continuum segment further comprises a plurality of second continuum spacer disks spaced at proximal side of the second continuum fixing disk; the dual continuum structural bone sequentially passes through the first continuum spacer disks, the rigid connection spacer disks and the second continuum spacer disks.

In the flexible surgical tool system, preferably, the linear motion mechanisms comprises five linear motion mechanisms: a first pair of the linear motion mechanisms connected with two pairs of the direction-controlling continuum structural bones, respectively, to achieve bending degrees of freedom in two directions for the first continuum segment; a second pair of the linear motion mechanisms connected with two pairs of the forceps structural bones, respectively, to achieve a rotational degree of freedom for two forceps rotators of the surgical effector; and a linear motion mechanism connected with a pair of the wrist structural bones to achieve a rotational degree of freedom for the wrist rotators of the surgical effector.

In the flexible surgical tool system, preferably, the direction-controlling continuum structural bone, the wrist structural bone, and the forceps structural bone pass through a guide disk via guide channels and are connected with the first sliding block and the second sliding block, respectively; a wrist structural bone guide hole and a forceps structural bone guide hole are respectively formed in the surgical effector base at two sides of the wrist rotator, and the wrist structural bone and the forceps structural bone pass through the wrist structural bone guide hole and the forceps structural bone guide hole, respectively.

The embodiments of present disclosure include the following advantages: 1. the disclosure provides a mechanical and a surgical effector arm based on a dual continuum mechanism. The dual continuum mechanism includes a first continuum segment, a rigid connection segment, and a second continuum segment in sequential association, and cooperates with a transmission driving unit. The transmission driving unit is associated with the rigid connection segment. The transmission driving unit is also associated with the surgical effector. Thus, the transmission driving unit can drive the dual continuum mechanism to bend in any direction and drive the surgical effector to rotate in a first plane and/or open or close in a second plane. 2. The two ends of the dual continuum structural bone in the dual continuum mechanism of the present disclosure are fixedly connected to the proximal end of the first continuum segment and the distal end of the second continuum segment. A length of the dual continuum structural bone remains unchanged in the driving process, so that total length of the first continuum segment, the rigid connection segment and the second continuum segment remains unchanged. When the transmission driving unit drives the first continuum segment to bend towards a certain direction, the coupling motion of the second continuum segment is also uniquely determined. 3. The disclosure provides a surgical effector at the end of the dual continuum mechanism. One end of the control wire of the surgical effector is connected with the wrist rotator and/or the forceps rotator, and the other end is connected with the transmission driving unit through steering pulleys. Therefore, the control of the wrist rotator and/or the forceps rotator of the surgical effector can be realized. 4. The transmission driving unit includes a double-threaded rod and a sliding block as a linear motion mechanism. When the double-threaded rod is driven to rotate, two sliding blocks matched with the double-threaded rod move linearly in opposite directions at the same speed, so as to drive the direction-controlling continuum structural bone, wrist structural bone or forceps structural bone connected with the sliding blocks to be pushed or pulled, so that the dual continuum mechanism can be bent towards any direction and the wrist rotator and/or forceps rotator of the surgical effector can rotate around the joint axis.

DETAILED DESCRIPTION

In order to make objectives, technical solutions, and advantages of the present disclosure clear, preferred embodiments of the present disclosure will be described in detail with reference to accompanying drawings. It is appreciated that embodiments shown in accompanying drawings are not limitations to the scope of the present disclosure but intended to explain the spirit of embodiments of the present disclosure.

Figure 1:
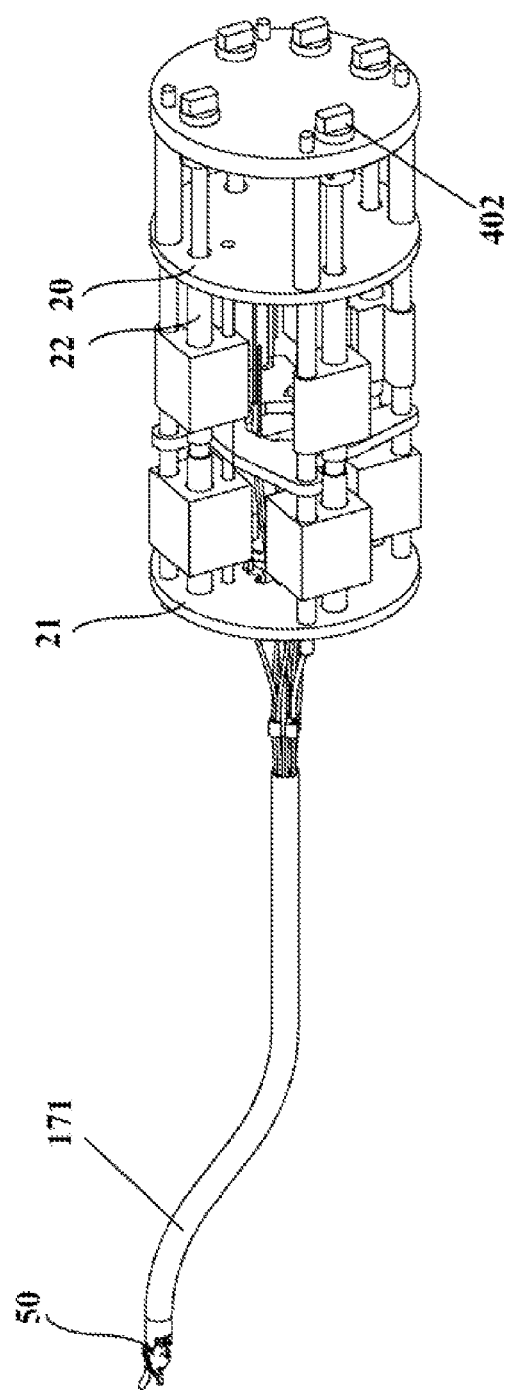
FIG. 1 is a schematic structural diagram of an overall structure of an embodiment according to the present disclosure.
Figure 2:
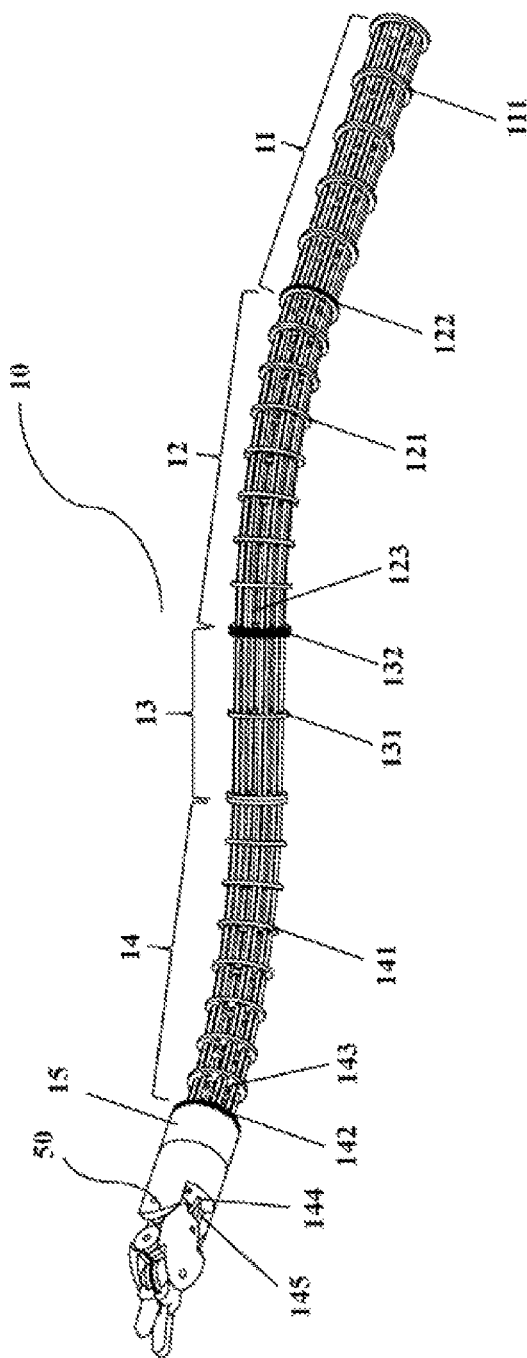
FIG. 2 is a schematic structural diagram of a mechanical arm based on a dual continuum mechanism according to the present disclosure.

As shown in FIGS. 1 and 2, the present embodiment provides a flexible surgical tool system including a mechanical arm 10. The mechanical arm 10 includes a first continuum segment 12, a rigid connection segment 13, and a second continuum segment 14. The first continuum segment 12, the rigid connection segment 13, and the second continuum segment 14 are sequentially associated to form a dual continuum mechanism. The flexible surgical tool system includes a surgical effector 50 connected at distal end of the second continuum segment 14 and a transmission driving unit 20. The transmission driving unit 20 is associated with the rigid connection segment 13 and the surgical effector 50, respectively, and operable to drive the first continuum segment 12 to bend in any direction to further drive the second continuum segment 14 to bend in an opposite direction, and to drive the surgical effector 50 to rotate in a first plane and/or open and close in a second plane.

Figure 3:
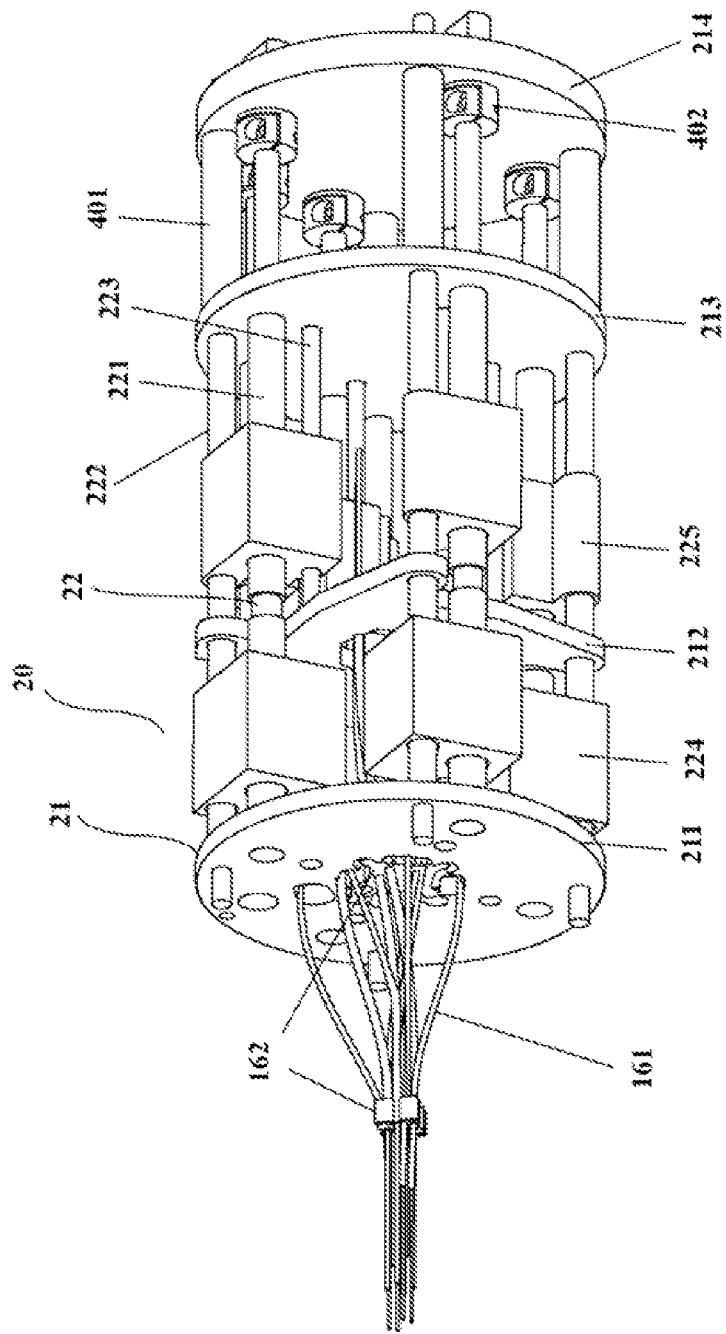
FIG. 3 is a structure of a transmission driving unit according to the present disclosure.

In the above embodiment, preferably, as shown in FIG. 3, the transmission driving unit 20 includes a plurality of linear motion mechanisms 22 operable to convert a rotational motion input to a linear motion output. The linear motion mechanism 22 includes: a double-threaded rod 221 that is rotatable and has two threaded sections thereon with threads in opposite directions; a first sliding block 224 and a second sliding block 225 respectively rotatably connected with two threaded sections of the double-threaded rod 221. When the double-threaded rod 221 rotates, the first sliding block 224 and the second sliding block 225 perform opposite linear motions along the double-threaded rod 221 at the same speed.

In the above embodiment, preferably, as shown in FIG. 2, the first continuum segment 12 includes a first continuum fixing disk 122 and direction-controlling continuum structural bones 123. The rigid connection segment 13 includes a rigid connection fixing disk 132, and the second continuum segment 14 includes a second continuum fixing disk 142 and dual continuum structural bones 143. Direction-controlling continuum structural bones 123 include a plurality of pairs. Distal ends of each pair of direction-controlling continuum structural bones 123 are connected with a rigid connection fixing disk 132, and proximal ends of each pair of direction-controlling continuum structural bones 123 pass through the first continuum fixing disk 122 and then are respectively connected with the first sliding block 224 and the second sliding block 225. There are a plurality of dual continuum structural bones 143. A distal end of each of the dual continuum structural bones 143 is connected with a second continuum fixing disk 142, and a proximal end is connected with the first continuum fixing disk 122 after passing through the rigid connection fixing disk 132. Thus, first sliding block 224 and second sliding block 225 which are in opposite linear motions can push and pull a pair of direction-controlling continuum structural bones 123 connected thereto, driving the first continuum segment 12 to bend in a certain direction, further driving the second continuum segment 14 to bend in opposite direction in a proportional relationship. Because a length of the dual continuum structural bone 143 remains unchanged during driving, a total length of the dual continuum mechanism including the first continuum segment 12, the rigid connection segment 13 and the second continuum segment 14 maintains unchanged. Thus, the coupling movement of the second continuum segment 14 is also uniquely determined.

In addition, the proportional relationship above is based on distribution radii of the dual continuum structural bones 143 in the first continuum segment 12 and the second continuum segment 14. In a preferred embodiment, the distribution radii of the first continuum segment 12 and the second continuum segment 14 are equal, so that the first continuum segment 12 and the second continuum segment 14 bend in an equivalently opposite manner, thereby ensuring that the first continuum fixing disk 122 and the second continuum fixing disk 142 are always parallel to each other during driving.

Figure 4:
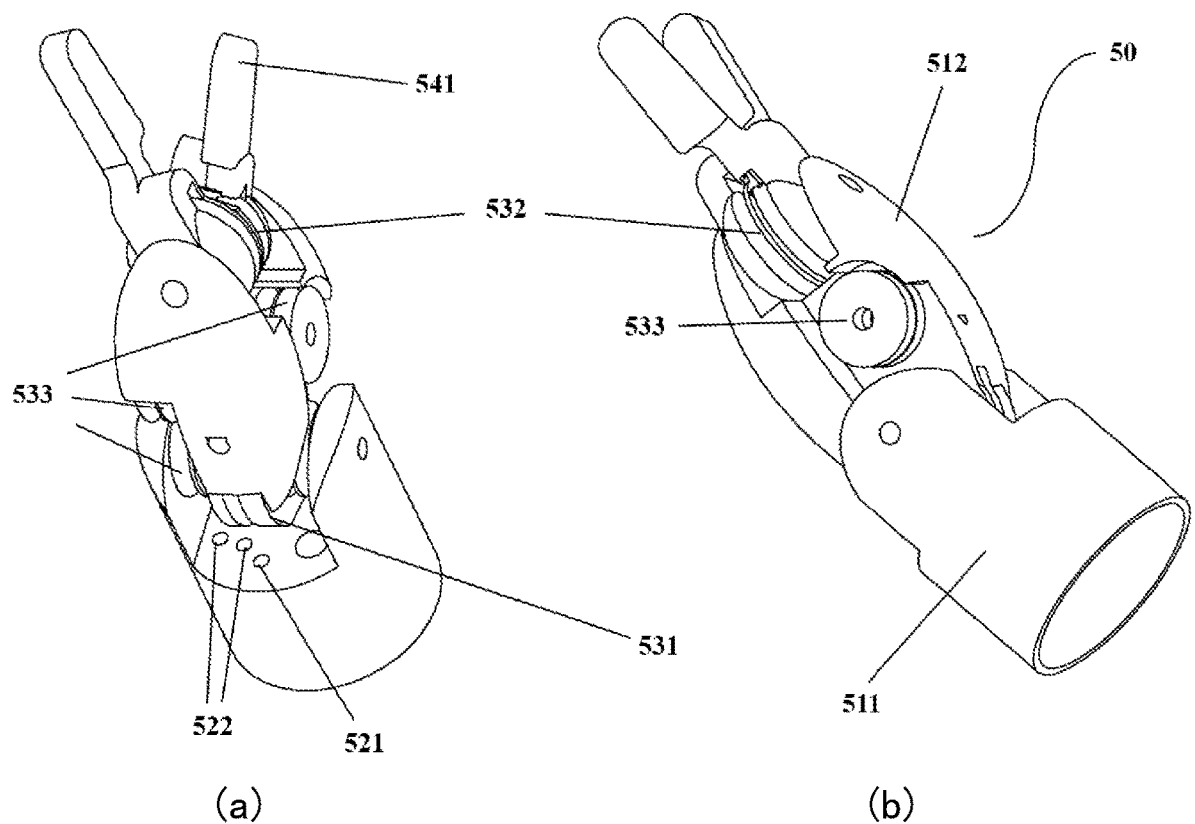
FIGS. 4 (a) and (b) are schematic structural diagrams of a surgical effector according to the present disclosure.
Figure 5:
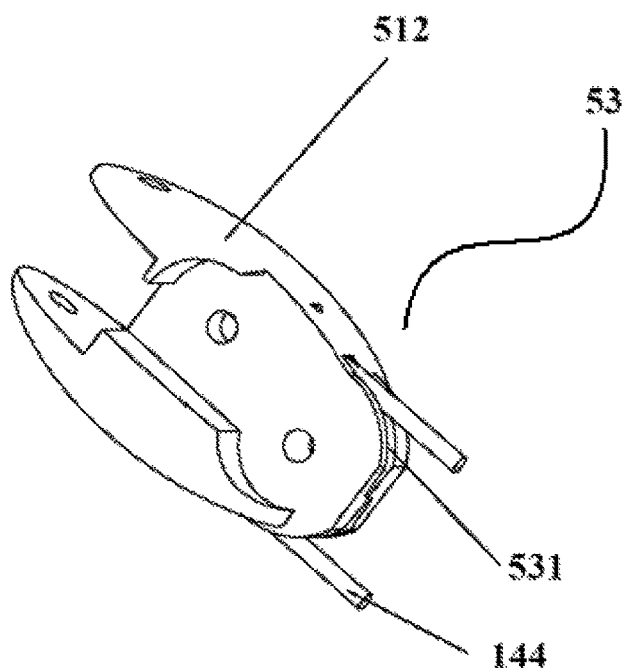
FIG. 5 is a schematic structural diagram of a wrist rotation mechanism according to the present disclosure.
Figure 6:
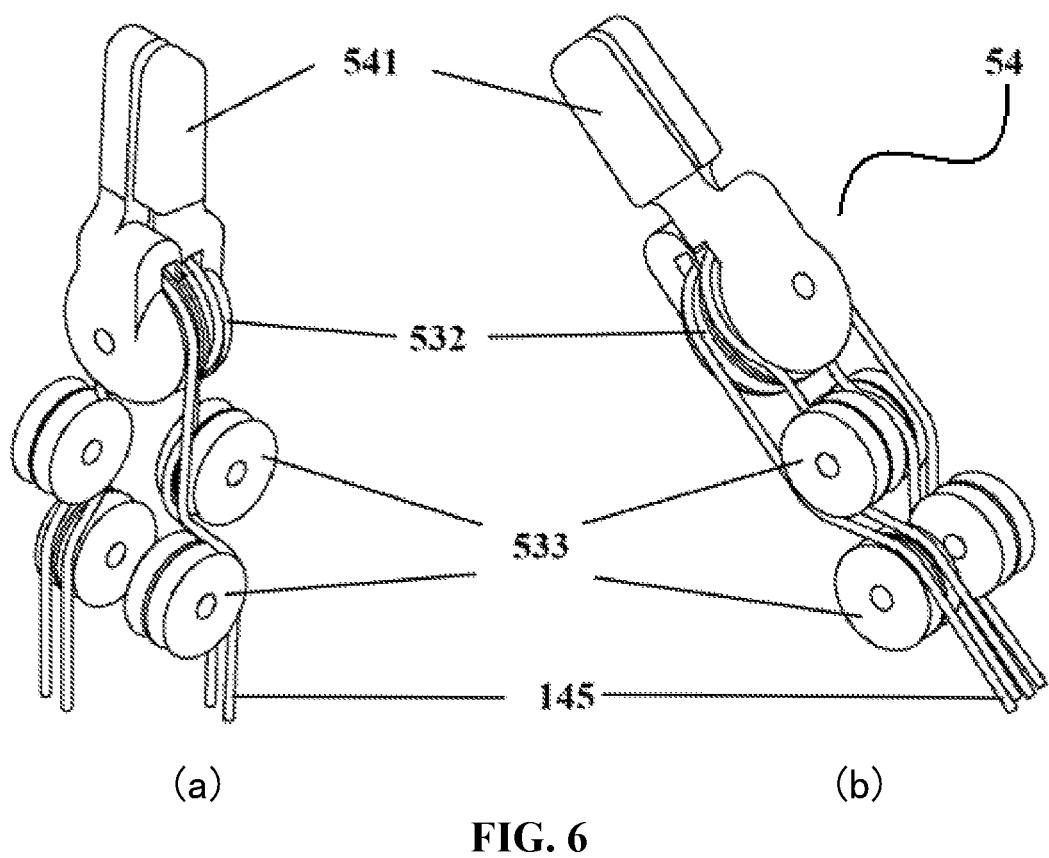
FIGS. 6 (a) and (b) are schematic structural diagrams of a forceps effector according to the present disclosure.

In the above embodiment, preferably, as shown in FIGS. 4-6, the surgical effector 50 includes: a surgical effector base 511 connected with distal end of the second continuum segment 14 via a surgical effector connection block 15; a wrist rotation mechanism 53 disposed on the surgical effector base 511 and associated with the linear motion mechanism 22 to perform a rotational motion in the first plane under the driving of the linear motion mechanism 22; a forceps effector 54 disposed on the wrist rotation mechanism 53 and associated with the linear motion mechanism 22. The forceps effector 54 can synchronously rotate with the wrist rotation mechanism 53 and perform opening and closing motions in the second plane under the driving of the linear motion mechanism 22.

In the above embodiment, preferably, as shown in FIGS. 4(*a*), 4(*b*), and 5, the wrist rotation mechanism 53 includes: a wrist rotator 531 rotatably connected with the surgical effector base 511; surgical effector housings 512 symmetrically mounted on both sides of the wrist rotator 531; a pair of wrist structural bones 144. A first end of one of the wrist structural bones 144 is connected with the first sliding block 224, and a second end sequentially passes through the first continuum segment 12, the rigid connection segment 13 and the second continuum segment 14 and is connected with a side of the wrist rotator 531. A first end of the other wrist structural bone 144 is connected to the second sliding block 225, and a second end sequentially passes through the first continuum segment 12, the rigid connection segment 13 and the second continuum segment 14 and is connected with another side of the wrist rotator 531. The first sliding block 224 and the second sliding block 225 which perform opposite linear motions push and pull the wrist structural bones 144 connected with the two sides of the wrist rotator 531 to drive the wrist rotator 531 to rotate forwards and backwards, so that the surgical effector housings 512 are driven to rotate in a first plane perpendicular to a rotation axis of the wrist rotator 531.

In the above embodiment, preferably, as shown in FIGS. 4(*a*), 4(*b*), 6(*a*), and 6(*b*), the forceps effector 54 includes: forceps rotators 532 rotatably connected between two surgical effector housings 512; effector jaws 541 integrally connected with the two forceps rotators 532, respectively; steering pulleys 533, multiple sets of steering pulleys 533 being rotatably connected between the two surgical effector housings 512; forceps structural bones 145. Two pairs of forceps structural bones 145 are provided. A first end of one forceps structural bone 145 of each pair is connected to the first sliding block 224, and a second end sequentially passes through the first continuum segment 12, the rigid connection segment 13 and the second continuum segment 14, is wound around a first set of steering pulleys 533 and connected with a side of the corresponding forceps rotator 532. A first end of the other forceps structural bone 145 is connected to the second sliding block 225, and a second end sequentially passes through the first continuum segment 12, the rigid connection segment 13 and the second continuum segment 14, is wound around the second set of steering pulleys 533 and connected with another side of the forceps rotator 532. The first sliding block 224 and the second sliding block 225 which move in opposite linear directions push and pull the forceps structural bones 145 connected with both sides of the forceps rotator 532, and with the steering of the steering pulleys 533, drive the two forceps rotator 532 to rotate forward and backward in opposite directions, so that the two effector jaws 541 are driven to perform opening and closing motion in a second plane perpendicular to a rotation axis of the forceps rotator 532.

In the above embodiment, preferably, as shown in FIG. 2, the mechanical arm 10 further includes a rigid feed segment 11. The rigid feed segment 11 includes a rigid feed segment spacer disk 111. A plurality of a rigid feed segment spacer disks 111 are spaced at the proximal side of the first continuum fixing disk 122. The first continuum segment 12 further includes a first continuum spacer disk 121. A plurality of first continuum spacer disks 121 are spaced between the distal side of the first continuum fixing disk 122 and the proximal side of the rigid connection fixing disk 132. The direction-controlling continuum structural bone 123, the wrist structural bone 144 and the forceps structural bone 145 sequentially passes through the rigid feed segment spacer disks 111 and the first continuum spacer disks 121 to prevent instability of the direction-controlling continuum structural bone 123, the wrist structural bone 144 and the forceps structural bone 145 when pushed. The rigid connection segment 13 further includes rigid connection spacer disk 131. A plurality of rigid connection spacer disks 131 are spaced at distal side of the rigid connection fixing disk 132. The second continuum segment 14 further includes second continuum spacer disk 141. A plurality of second continuum spacer disks 141 are spaced at proximal side of the second continuum fixing disk 142. The dual continuum structural bone 143 sequentially passes through the first continuum spacer disks 121, the rigid connection spacer disks 131, and the second continuum spacer disks 141 to limit the dual continuum structural bone 143.

In the above embodiment, preferably, as shown in FIG. 3, the transmission driving unit 20 further includes a base frame 21. The base frame 21 includes a first support plate 211 and a second support plate 213 spaced apart from each other. The double-threaded rod 221 is axially rotatably connected with the first support plate 211 and the second support plate 213. A first guide rod 222 and a second guide rod 223 are axially connected between the first support plate 211 and the second support plate 213. The first sliding block 224 and the second sliding block 225 are slidably connected with the first guide rod 222 and the second guide rod 223, respectively. The first guide rod 222 and the second guide rod 223 have limiting and guiding functions to enable the first sliding block 224 and the second sliding block 225 to smoothly perform opposite linear motions.

In above embodiment, preferably, the base frame 21 further includes a connection plate 212 disposed between the first support plate 211 and the second support plate 213 and connected with the second guide rod 223. The double-threaded rod 221 passes through the connection plate 212 and has a gap therebetween. The connection plate 212 can separate the two threaded sections of the double-threaded rod 221. The base frame 21 further includes a third support plate 214 connected with the second support plate 213 via a first guide rod 222, so that an arrangement space for other required electrical components is formed between the second support plate 213 and the third support plate 214.

In above embodiment, preferably, a positioning sleeve 401 can be disposed over the first guide rod 222 and/or the second guide rod 223 to position the connection plate 212 and/or the third support plate 214. Alternatively, the first support plate 211 and the second support plate 213 may be fixedly connected by a threaded support rod, and positioning nuts cooperatively connected with the support rod can position the first support plate 211, the second support plate 213 and the connection plate 212. Therefore, the positioning sleeve 401 can be replaced with the positioning nuts.

In above embodiment, preferably, there are five linear motion mechanisms 22. A first pair of linear motion mechanisms 22 are connected with two pairs of direction-controlling continuum structural bones 123, respectively, to achieve the bending degrees of freedom in two directions for the first continuum segment 12. A second pair of linear motion mechanisms 22 are connected with two pairs of the forceps structural bones 145, respectively, to achieve rotational degree of freedom of the two forceps rotators 532 of the surgical effector 50. And a linear motion mechanism 22 is connected with a pair of wrist structural bones 144 to achieve rotational degree of freedom of a wrist rotator 531 of the surgical effector 50.

In the above embodiment, preferably, as shown in FIG. 3, the direction-controlling continuum structural bone 123, the wrist structural bone 144, and the forceps structural bone 145 pass through a guide plate 162 via guide channel 161 and are connected with the first sliding block 224 and the second sliding block 225, respectively. As shown in FIG. 4(a), a wrist structural bone guide hole 521 and a forceps structural bone guide hole 522 are respectively formed in the surgical effector base 511 at two sides of the wrist rotator 531. The wrist structural bone 144 and the forceps structural bone 145 respectively pass through the wrist structural bone guide hole 521 and the forceps structural bone guide hole 522.

In the above embodiment, preferably, as shown in FIG. 3, the double-threaded rod 221 is connected with a coupling male connector 402 mounted on the third support plate 214, and then, with the driving motor shaft via the coupling female connector.

Figure 7:
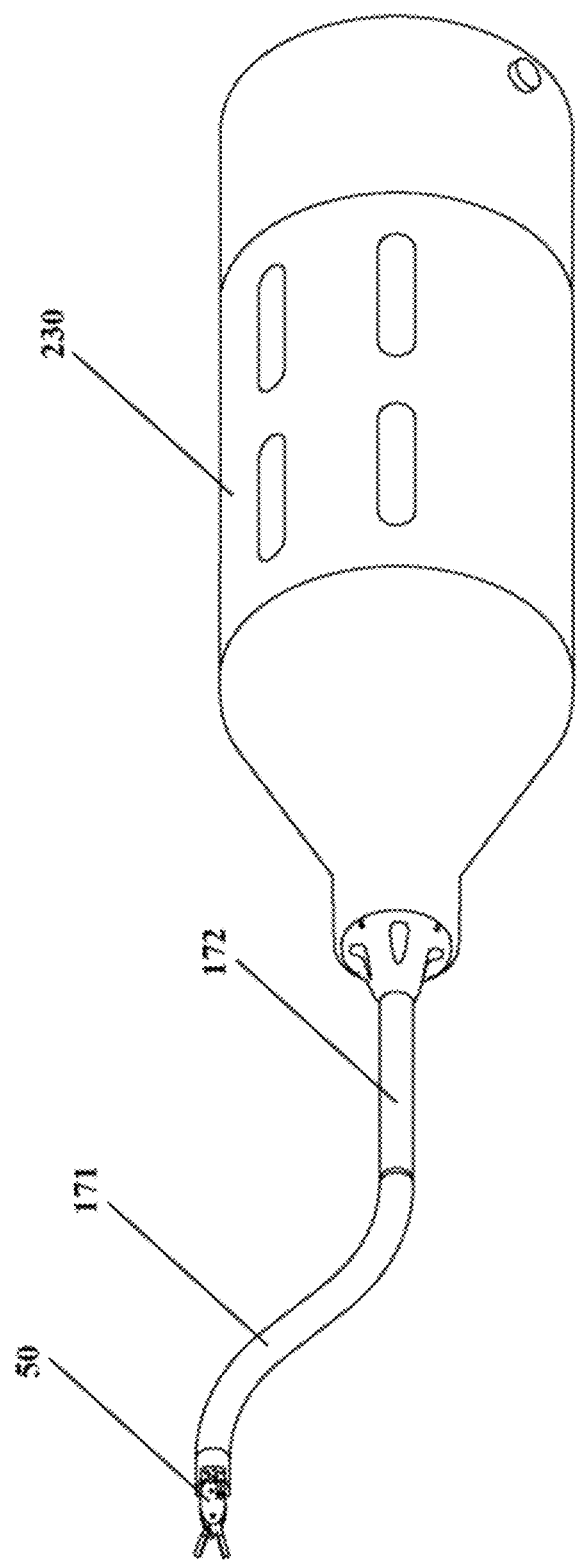
FIG. 7 is a schematic structural diagram of an embodiment with a housing, an envelope and an outer sleeve according to the present disclosure.

In the above embodiment, preferably, as shown in FIG. 7, a housing 230 is provided outside the transmission driving unit 20. The first support plate 211 and the second support plate 213 are both connected with the housing 230. An envelope 171 is provided outside the mechanical arm 10 to improve the smoothness of the mechanical arm 10 entering a natural orifice or a surgical incision of a human body. In addition, an outer sleeve 172 can also be provided outside the envelope 171.

The disclosure is only described with reference to the embodiments above. The structure, the arrangement position and the connection of each component can be changed. On the basis of the technical solutions of the disclosure, improvement and equivalent transformation of individual components according to the principle of the disclosure are not excluded from the protection scope of the disclosure.

The invention claimed is:

1. A flexible surgical tool system comprising:
 a mechanical arm (10) comprising a first continuum segment (12), a rigid connection segment (13), and a second continuum segment (14), the first continuum segment (12) and the second continuum segment (14) being sequentially associated to form a dual continuum mechanism;
 a surgical effector (50) connected at a distal end of the second continuum segment (14); and
 a transmission driving unit (20) associated with the rigid connection segment (13) and with the surgical effector (50), respectively, and operable to drive the first continuum segment (12) to bend in any direction to drive the second continuum segment (14) to bend in an opposite direction, and to drive the surgical effector (50) to rotate in a first plane and/or open and close in a second plane;

wherein the transmission driving unit (20) comprises a plurality of linear motion mechanisms (22), each linear motion mechanism comprising a double-threaded rod (221), a first sliding block (224), and a second sliding block (225);

the surgical effector (50) comprises a wrist rotation mechanism (53);

the plurality of linear motion mechanisms (22) comprise a first linear motion mechanism, the first linear motion mechanism comprising a first double-threaded rod, a first wrist sliding block, and a second wrist sliding block;

wherein the wrist rotation mechanism (53) mounted at the distal end of the second continuum segment (14) and associated with the first linear motion mechanism and driven by the first linear motion mechanism to perform a rotational motion in the first plane;

wherein the wrist rotation mechanism (53) comprises:

a wrist rotator (531);

a pair of wrist structural bones (144), the first linear motion mechanism connected with the pair of the wrist structural bones (144) to achieve a rotational degree of freedom for the wrist rotators (531) of the surgical effector (50);

wherein a first end of one of the pair of wrist structural bones (144) is connected with the first wrist sliding block, a second end sequentially passes through the first continuum segment (12), the rigid connection segment (13) and the second continuum segment (14) and is connected with a side of the wrist rotator (531), a first end of the other of the pair of wrist structural bones (144) is connected with the second wrist sliding block, and a second end of the other of the pair of wrist structural bones (144) sequentially passes through the first continuum segment (12), the rigid connection segment (13) and the second continuum segment (14) and is connected with another side of the wrist rotator (531).

2. The flexible surgical tool system of claim 1, wherein the first continuum segment (12) comprises a first continuum fixing disk (122) and a plurality of pairs of direction-controlling continuum structural bones (123), and the rigid connection segment (13) comprises a rigid connection fixing disk (132); and distal ends of each pair of direction-controlling continuum structural bones (123) are connected with the rigid connection fixing disk (132), and proximal ends of each pair of direction-controlling continuum structural bones (123) pass through the first continuum fixing disk (122) and are connected with the first sliding block (224) and the second sliding block (225), respectively.

3. The flexible surgical tool system of claim 2, wherein the second continuum segment (14) comprises a second continuum fixing disk (142) and a plurality of dual continuum structural bones (143); and a distal end of each dual continuum structural bone (143) is connected with the second continuum fixing disk (142), and the proximal end of each dual continuum structural bone (143) passes through the rigid connection fixing disk (132) and is connected with the first continuum fixing disk (122).

4. The flexible surgical tool system of claim 3, wherein the rigid connection segment (13) further comprises a plurality of rigid connection spacer disks (131) spaced at distal side of the rigid connection fixing disk (132);

the second continuum segment (14) further comprises a plurality of second continuum spacer disks (141) spaced at proximal side of the second continuum fixing disk (142); and the dual continuum structural bone (143) sequentially passes through the first continuum spacer disks (121), the rigid connection spacer disks (131) and the second continuum spacer disks (141).

5. The flexible surgical tool system of claim 2, wherein the surgical effector (50) further comprises:

a forceps effector (54) mounted on the wrist rotation mechanism (53) and associated with the plurality of linear motion mechanisms (22), the forceps effector (54) being driven by the plurality of linear motion mechanisms (22) to perform opening or closing motion in the second plane.

6. The flexible surgical tool system of claim 5, wherein the surgical effector (50) further comprises:

a surgical effector base (511) connected at distal end of the second continuum segment (14) via a surgical effector connection block (15), the wrist rotation mechanism (53) being mounted on the surgical effector base (511).

7. The flexible surgical tool system of claim 6, wherein the wrist rotator (531) is rotatably connected with the surgical effector base (511);

the wrist rotation mechanism (53) further comprises:

surgical effector housings (512) symmetrically mounted on both sides of the wrist rotator (531).

8. The flexible surgical tool system of claim 7, wherein the forceps effector (54) comprises:

a pair of forceps rotators (532) rotatably connected between the surgical effector housings (512);

a pair of effector jaws (541) integrally connected with the pair of forceps rotators (532), respectively;

a first and a second sets of steering pulleys (533) rotatably connected between the surgical effector housings (512);

a first and a second pairs of forceps structural bones (145), wherein a first end of one forceps structural bone (145) of each pair is connected with the first sliding block (224), a second end sequentially passes through the first continuum segment (12), the rigid connection segment (13) and the second continuum segment (14), is wound around the first set of steering pulleys (533) and connected with a side of a corresponding forceps rotator (532), and wherein a first end of the other forceps structural bone (145) is connected with the second sliding block (225), and a second end sequentially passes through the first continuum segment (12), the rigid connection segment (13) and the second continuum segment (14), is wound around the second set of steering pulleys (533) and is connected with another side of the corresponding forceps rotator (532).

9. The flexible surgical tool system of claim 8, wherein the mechanical arm (10) further comprises a rigid feed segment (11) comprising a plurality of rigid feed segment spacer disks (111) spaced at proximal side of the first continuum fixing plate (122);

the first continuum segment (12) further comprises a plurality of first continuum spacer disks (121) spaced between a distal side of the first continuum fixing disk (122) and a proximal side of the rigid connection fixing disk (132); and the plurality of pairs of direction-controlling continuum structural bones (123), the pairs of wrist structural bones (144) and the first and second pairs of forceps structural bones (145) sequentially pass through the rigid feed segment spacer disks (111) and the first continuum spacer disks (121).

10. The flexible surgical tool system of claim 8, wherein the plurality of pairs of direction-controlling continuum structural bones (123) comprise two pairs of direction-controlling continuum structural bones, the plurality of linear motion mechanisms (22) comprise:

a second linear motion mechanism and a third linear motion mechanism connected with the two pairs of direction-controlling continuum structural bones, respectively, to achieve bending degrees of freedom in two directions for the first continuum segment (12).

11. The flexible surgical tool system of claim 8, wherein the plurality of pairs of direction-controlling continuum structural bones (123), the pair of wrist structural bones (144), and the first and second pairs of forceps structural bones (145) pass through a guide disk (162) via guide channels (161) and are connected with the first sliding block (224) and the second sliding block (225), respectively.

12. The flexible surgical tool system of claim 8, wherein the plurality of linear motion mechanisms (22) comprise:

a fourth linear motion mechanism and a fifth linear motion mechanism connected with the first and second pairs of the forceps structural bones (145), respectively, to achieve a rotational degree of freedom for the pair of forceps rotators (532) of the surgical effector (50).

13. The flexible surgical tool system of claim 8, wherein the surgical effector (50) further comprises:

a wrist structural bone guide hole (521) formed in the surgical effector base (511) at two sides of the wrist rotator (531), the wrist structural bone (144) pass through the wrist structural bone guide hole (521).

14. The flexible surgical tool system of claim 8, wherein the surgical effector (50) further comprises:

a forceps structural bone guide hole (522) formed in the surgical effector base (511) at two sides of the wrist rotator (531), the first and second pairs of forceps structural bones (145) pass through the forceps structural bone guide hole (522).

* * * * *